United States Patent
Boyd et al.

(10) Patent No.: US 9,440,031 B2
(45) Date of Patent: Sep. 13, 2016

(54) DRUG DELIVERY DEVICE

(75) Inventors: Malcolm Stanley Boyd, Wellsbourne (GB); Robert Veasey, Leamington Spa (GB); David Plumptre, Droitwich Spa (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 125 days.

(21) Appl. No.: 13/140,132

(22) PCT Filed: Dec. 21, 2009

(86) PCT No.: PCT/EP2009/067605
§ 371 (c)(1),
(2), (4) Date: Oct. 11, 2011

(87) PCT Pub. No.: WO2010/072694
PCT Pub. Date: Jul. 1, 2010

(65) Prior Publication Data
US 2012/0029442 A1 Feb. 2, 2012

(30) Foreign Application Priority Data
Dec. 23, 2008 (EP) .................................... 08022316

(51) Int. Cl.
*A61M 5/32* (2006.01)
*A61M 5/34* (2006.01)
(Continued)

(52) U.S. Cl.
CPC .............. *A61M 5/3202* (2013.01); *A61M 5/24* (2013.01); *A61M 5/3129* (2013.01); *A61M 5/347* (2013.01); *A61M 2005/2407* (2013.01); *A61M 2205/276* (2013.01)

(58) Field of Classification Search
CPC .. A61M 5/3202; A61M 5/24; A61M 5/3129; A61M 5/347; A61M 2005/2407; A61M 2205/276
USPC ................................ 604/197, 189, 181, 232
See application file for complete search history.

(56) References Cited

U.S. PATENT DOCUMENTS 4,935,012 A 6/1990 Magre et al.
5,087,249 A 2/1992 Deal
(Continued)

FOREIGN PATENT DOCUMENTS

DE 9116035 3/1992
EP 0904790 3/1999
(Continued)

OTHER PUBLICATIONS

International Preliminary Report on Patentability for International App. No. PCT/EP2009/067605, dated Jun. 29, 2011.
(Continued)

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

The present invention relates to drug delivery devices. The drug delivery device according to the invention includes a housing with a needle holder suitable for attaching a needle unit to the housing at the distal end, and a cap being capable of covering the distal end of the drug delivery device and comprising a retaining member capable of securing the cap by engaging with the housing, the retaining member is prevented from engaging with the housing with the needle unit being attached to the needle holder. Furthermore, using a cap for covering the distal end of the drug delivery device is disclosed.

16 Claims, 3 Drawing Sheets

(51) Int. Cl.
*A61M 5/31* (2006.01)
*A61M 5/24* (2006.01)

(56) References Cited

U.S. PATENT DOCUMENTS

| | | | | |
|---|---|---|---|---|
| 5,997,513 | A * | 12/1999 | Smith | A61M 5/3202 |
| | | | | 128/919 |
| 6,196,998 | B1 * | 3/2001 | Jansen et al. | 604/111 |
| 6,454,746 | B1 * | 9/2002 | Bydlon | A61M 5/3137 |
| | | | | 604/227 |
| 7,147,624 | B2 * | 12/2006 | Hirsiger | A61M 5/326 |
| | | | | 604/192 |
| 8,118,788 | B2 * | 2/2012 | Frezza | A61M 5/3134 |
| | | | | 604/111 |
| 2002/0133122 | A1 | 9/2002 | Giambattista et al. | |
| 2003/0191438 | A1 | 10/2003 | Ferguson et al. | |
| 2005/0277895 | A1 | 12/2005 | Giambattista et al. | |
| 2007/0173772 | A1 | 7/2007 | Liversidge | |
| 2007/0293818 | A1 | 12/2007 | Stout et al. | |
| 2008/0108951 | A1 | 5/2008 | Jerde et al. | |
| 2008/0140016 | A1 * | 6/2008 | Heinz | A61M 5/347 |
| | | | | 604/203 |
| 2008/0154192 | A1 * | 6/2008 | Schraga | A61M 5/50 |
| | | | | 604/110 |

FOREIGN PATENT DOCUMENTS

| | | |
|---|---|---|
| EP | 1923084 | 5/2008 |
| FR | 2687073 | 8/1993 |
| WO | 2006/032385 | 3/2006 |

OTHER PUBLICATIONS

International Preliminary Report on Patentability for International Application No. PCT/EP2009/067605, dated Jul. 7, 2011.
European Search Report for EP App. No. 08022316, dated May 29, 2009.
International Search Report for Int. App. No. PCT/EP2009/067606, mailed Jun. 7, 2010.

* cited by examiner

FIG 1
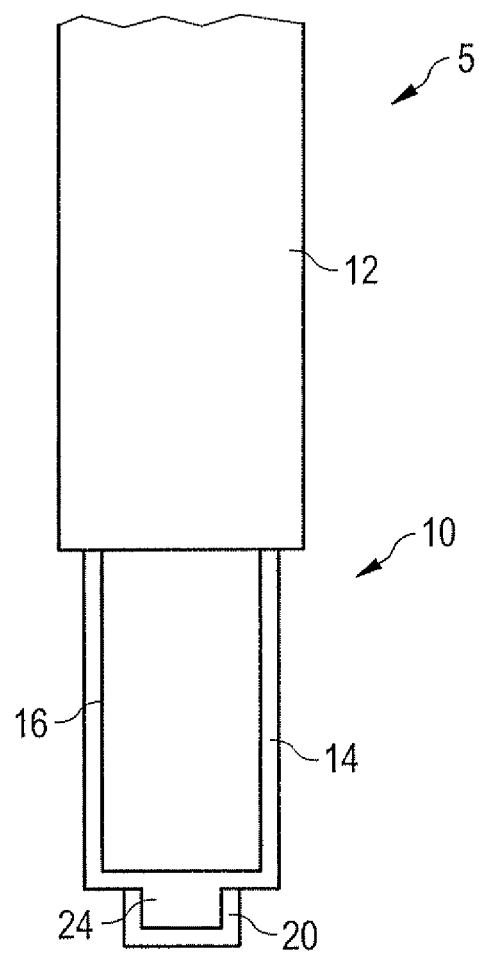
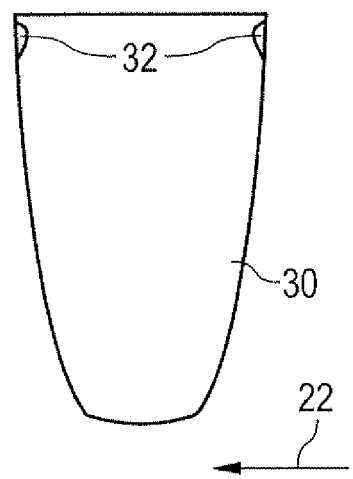

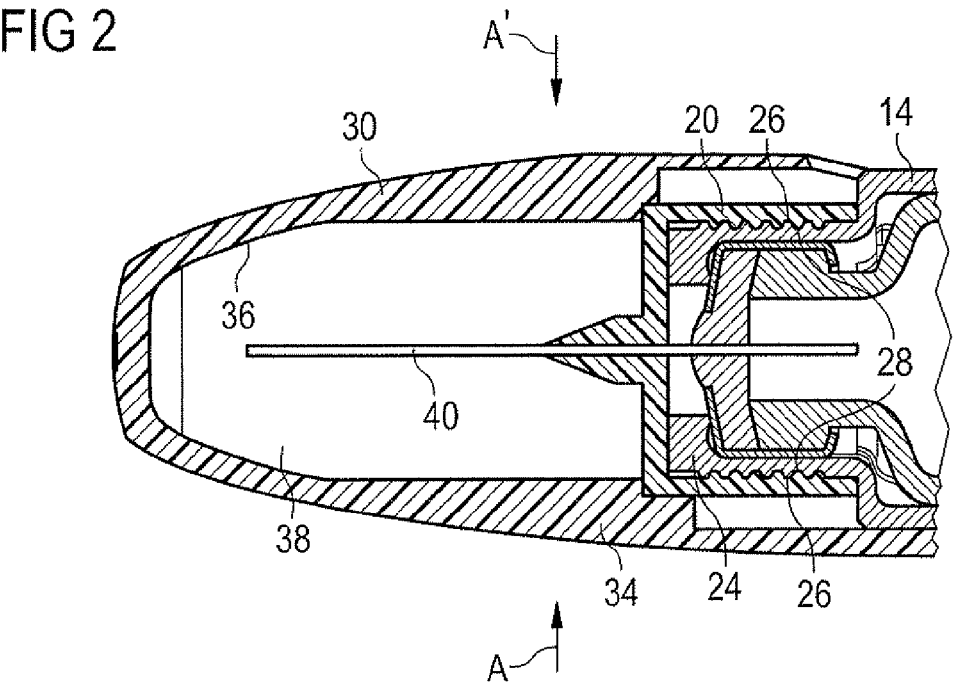
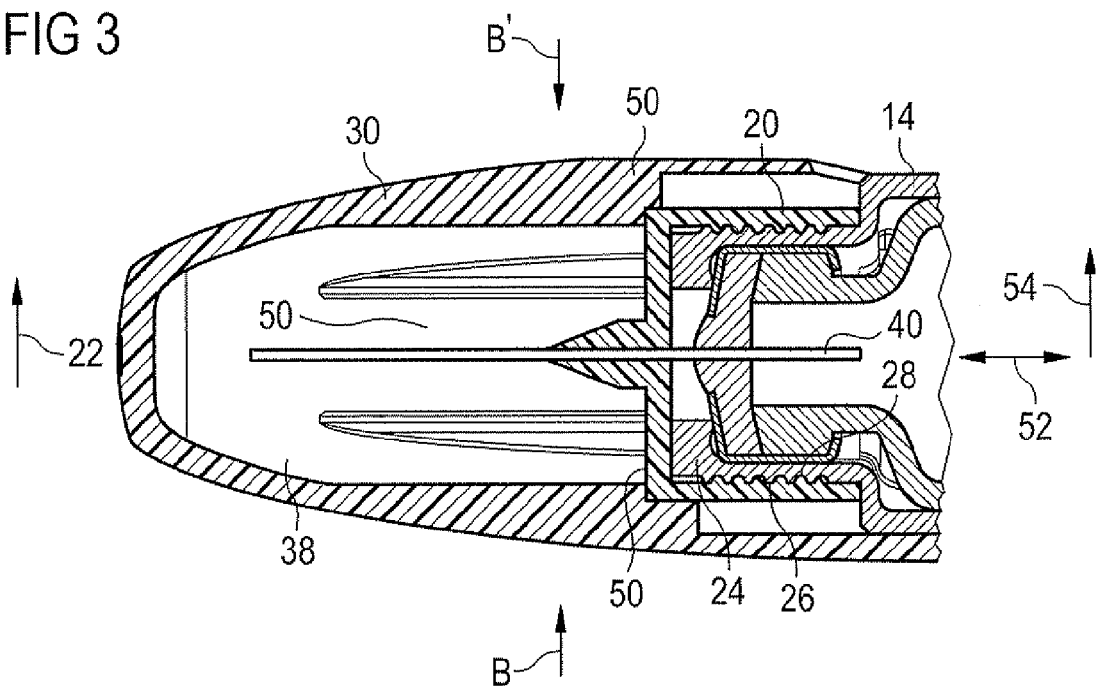

DRUG DELIVERY DEVICE

CROSS REFERENCE TO RELATED APPLICATIONS

The present application is a U.S. National Phase application pursuant to 35 U.S.C. §371 of International Application No. PCT/EP2009/067605 filed Dec. 21, 2009, which claims priority to EP Patent Application No. 08022316.7 filed on Dec. 23, 2008. The entire disclosure contents of these applications are herewith incorporated by reference into the present application.

FIELD OF THE INVENTION

The present invention relates to drug delivery devices. Furthermore, the present invention relates to using a cap for covering a distal end of a drug delivery device.

BACKGROUND

Drug delivery devices are generally known for the administration of a medicinal product, for example insulin, growth hormones or other drugs suitable for self-administration. Some drug delivery devices are configured to deliver a plurality of doses. Additionally, some drug delivery devices are configured to allow setting of different dose sizes which are to be delivered.

In the document EP-A1-1923084, a drug delivery device is shown where a user may activate the drug delivery device. The drug delivery device includes a drive mechanism suitable for use in pen-type injectors, wherein a number of pre-set doses of medicinal product can be administered. A needle unit can be attached to the drug delivery device for dispensing the medicinal product into a patient's skin. After usage of the drug delivery device, the distal end of the device can be covered by a cap.

It is generally advisable that a needle unit is removed after using the drug delivery device and that the drug delivery device is covered by a cap after usage so as to prevent contact with the needle and/or contamination of the device.

In US 2003/0191438 A1 a medical needle shield is shown that includes a shield being extensible from a retracted position to an extended position, wherein the shield includes a first segment mounted to a medical needle device having a needle extending from the device, whereby a further segment substantially encloses a distal end of the needle.

In U.S. Pat. No. 4,935,012 a safety device for protecting medical personnel and the like against needle stick injuries and/or exposure to communicable diseases or other harmful agents is shown. The safety device comprises an elongated protective sleeve supported by front and rear bearing members for sliding movement about a medical needle and its associated support structure.

Further safety shield systems for pen needles are known from the documents US 2002/0133122 A1 and US 2007/0293818 A1.

SUMMARY

It is an aim of the present invention to provide for an improved drug delivery device. In particular, a drug delivery device should be provided, which encourages a user to remove the needle after operation of the device.

For this aim, a drug delivery device comprises a housing with a needle holder suitable for attaching a needle unit to the housing at the distal end, and a cap being capable of covering the distal end of the drug delivery device and comprising a retaining member capable of securing the cap by engaging with the housing, the retaining member is prevented from engaging with the housing with the needle unit being attached to the needle holder.

In particular, the cap may be configured to be capable of covering the distal end of the drug delivery device. The cap may be a unitary part. The cap may be a single injection moulded piece. The retaining member may be configured to be capable of securing the cap by engaging with the housing. The retaining member may be configured to secure the cap to the housing.

In such a drug delivery device, the engagement of the retaining members of the cap with the housing is prevented when the needle unit is attached to the drug delivery device. Consequently, a user experiences a feedback when attempting to place the cap on the drug delivery device. This is achieved by preventing the retaining member from engaging with the housing as long as the needle unit is attached to the needle holder.

Furthermore, the risk of needle stick injuries is reduced because the cap has features which abut the needle unit before the needle cannula risks piercing the distal end of the cap.

In a first embodiment, the cap comprises at least one protruding element on the inner surface of the cap, wherein the protruding element is configured to abut or abuts the needle unit so as to prevent the retaining member from engaging with the housing.

The at least one protruding element on the inner surface can abut the needle unit while attempting to place the cap on the drug delivery device. The arrangement of the protruding element is chosen such that the retaining members of the cap are prevented from engaging with respect to the housing, as the cap can not reach its final position. The at least one protruding element on the inner surface effectively stops further engagement of the cap with the housing by abutting the needle unit. In addition, the cap can be designed such that a relatively short cap is suitable for both long and short needle cannula. This can be achieved, for example, by placing the at least one protruding element on the inner surface close to an end of the cap which faces the proximal end.

In a further embodiment, the at least one protruding element is formed as a step along the inner side wall of the cap.

According to this embodiment, the protruding element can be easily implemented into a cap. Hence, the design of the cap is simplified and conventional techniques can be employed for producing the cap. For example, the cap can be provided as a single injection moulded piece fabricated from thermoplastic materials, e.g. polypropylene, polystyrene, polyamide, polyethylene, or the like. The cap may be a unitary or one-piece cap.

In one embodiment, the at least one protruding element is formed as at least one rib or bar on the inner side wall of the cap. The at least one rib or bar may be arranged along a longitudinal axis being arranged between the distal end and the proximal end of the cap.

In this example, the protruding element provides for a reinforcement of the cap by strengthening the cap on the inner surface. Accordingly, the manufacturability of the drug delivery device is facilitated as rather thin side walls of the cap can be employed. In addition, the cap according to this example can be implemented as a single injection moulded piece without the need for performing significant design changes to a conventional cap.

According to a further embodiment, the at least one rib on the inner side wall of the cap is capable of providing guidance when attempting to engage the cap on the housing.

The rib of the cap can be arranged such that it fits into respective grooves on the housing or the needle holder when attempting to engage the cap on the housing. Hence, the rib provides an orientation feature which prevents the user from placing the cap with a false orientation with respect to the housing. Rotation of the cap with respect to the housing may be prevented by means of mechanical cooperation of the rib and the respective groove. It should be noted that it is within the scope of the invention to provide a plurality of ribs. In addition, the plurality of ribs on the inner surface of the cap can be implemented such that a single orientation or a plurality of orientations of the cap with respect to the housing is possible.

In a further embodiment, needle connection means are provided which allow the attachment of the needle unit to the needle holder by rotating one relative to the other.

The needle holder may comprise an outer thread, the outer thread being capable of engaging with a corresponding inner thread of the needle unit According to another embodiment, the needle connection means comprise a bayonet connection.

A needle holder and a needle unit of this kind can be easily implemented in drug delivery devices. Furthermore, attaching the needle unit is simplified as the corresponding threads offer a simple mechanical connection. Due to the threaded connection, the outer diameter of the needle unit is significantly larger when compared to the outer diameter of the needle holder. Consequently, the protruding element or the protruding elements can be adapted to the space occupied by the needle unit around the needle holder in a radial direction. Accordingly, the design of the cap can be adapted for different kinds of needle units.

In one embodiment, the protruding element is arranged such that it contacts the needle unit in a region between the outer diameter of the needle holder and the outer diameter of the needle unit.

The actual design of the cap is independent of the precise dimensions of the needle unit, as long as the protruding element is capable of contacting the needle unit in a region between the outer diameter of the needle holder and the outer diameter of the needle unit. Accordingly, different types of needle units can be employed, which can in addition be suitable for accommodating long or short needles.

In one embodiment, the protruding element abuts a front side of the needle unit facing the distal end of the drug delivery device when the needle unit is attached to the needle holder.

According to this embodiment, the design of the cap is independent from the outer diameter of the needle holder and the outer diameter of the needle unit. Consequently, a wide range of different needle units can be used for such a drug delivery device. In order to accommodate a long needle cannula, a correspondingly long cap should be used.

During placement of the cap on the housing, the danger of needle stick injuries is reduced by providing a cavity in which the needle is located. The cavity is capable of surrounding the needle unit without abutting the needle cannula of the needle unit on its inner surface when attempting to engage the cap on the housing. The cavity may be configured to surround the needle unit without abutting the needle cannula.

In one embodiment, the retaining member of the cap is arranged at the end of the cap facing the proximal end of the housing.

In this embodiment, the retaining member can be provided in a region of the cap which can be fabricated from relatively flexible material. This allows the engagement of the cap with the housing requiring only a relatively weak force which needs to be applied by the user. Accordingly, operability of the drug delivery device is enhanced.

According to a further embodiment, the retaining member is capable of engaging into a corresponding mating retaining member on the housing.

In this example, the retaining member can be fabricated as a pair of mating means which allow an easy implementation, in particular when providing the cap as a single injection moulded piece. Accordingly, the manufacturability of the drug delivery device is simplified.

According to a further embodiment, the retaining member and the corresponding mating retaining member comprise a clip feature or a clamp capable of engaging in a corresponding recess.

This allows a simple fixture of the cap with respect to the housing.

According to a further embodiment, the cap comprises at least one protrusion being arranged on an end face of the cap.

In this example, the cap can be implemented such that the protrusion fits into a corresponding part of the housing. Hence, orientation of the cap with respect to the housing can be defined by the protrusion. Rotation of the cap with respect to the housing may be prevented in this way.

According to a further embodiment, the cap comprises two protrusions which are located at symmetric positions around a longitudinal axis being arranged between the distal end and the proximal end of the cap.

In this example, the number of possible orientations of the cap with respect to the housing is reduced which facilitates engaging the cap with the housing. Furthermore, the user is encouraged to place the cap with two possible orientations only. Consequently, an engagement of the cap by the user in arbitrary positions relative to the housing is prevented.

According to a further embodiment, the housing comprises a cartridge holder capable of enclosing a cartridge containing a medicament and wherein the cap can be attached such that it covers at least a part of the cartridge holder.

In this example, the housing comprises a cartridge holder which can be fabricated as a separate piece together with a body wherein a drive mechanism can be arranged. Accordingly, the manufacturability of the drug delivery device is facilitated.

For the above mentioned aim, a cap is used for covering the distal end of the drug delivery device having a housing with a needle holder suitable for attaching a needle unit at the distal end of the housing, the cap comprising a retaining member capable of securing the cap by engaging with the housing, the retaining member is prevented from engaging with the housing with the needle being attached to the needle holder.

BRIEF DESCRIPTION OF THE FIGURES

Other features will become apparent from the following detailed description when considered in conjunction with the accompanying drawings.

In the drawings:

FIG. 1 schematically shows a simplified side view of a drug delivery device according to an embodiment;

FIG. 2 schematically shows a simplified cross sectional side view of a drug delivery device according to an embodiment;

FIG. 3 schematically shows a simplified cross sectional side view of a drug delivery device according to an embodiment;

DETAILED DESCRIPTION

Figure 4:
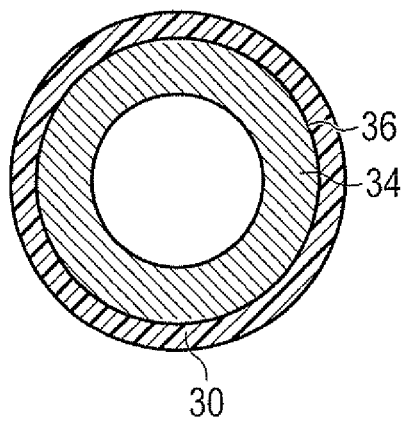
FIG. 4 schematically shows a cross sectional view of a part of a drug delivery device according to an embodiment.

In FIG. 1 an embodiment of a drug delivery device 5 is shown, which is an injector for a liquid medication. The drug delivery device 5 may be configured to deliver a plurality of fixed or user-settable doses of a drug. The drug delivery device 5 may be a pen-type device. The drug delivery device 5 comprises a housing 10, which can be formed from a single or multiple pieces.

In the embodiment shown in FIG. 1, the housing 10 comprises a body 12 and a cartridge holder 14, wherein a cartridge 16 containing a medical product or drug can be located. The cartridge holder 14 may be secured against movement with respect to the body 12. A needle unit 20 is located at the distal end 22 of the drug delivery device 5. The needle unit 20 may be secured against movement with respect to the cartridge holder 14. As will be shown below, needle unit 20 can be secured to a needle holder 24 which forms part of the cartridge holder 14 by a threaded engagement. Through needle unit 20 the medical product can be injected into a patient.

Delivery of the medical product can be performed by means of a piston rod or the like (not explicitly shown), which can be moved into the distal direction with respect to the cartridge 16. A piston (not explicitly shown) which is retained in the cartridge 16 and seals the cartridge 16 on the proximal end side may be moved in the distal direction with respect to the cartridge 16 by the piston rod. The cartridge holder 14 can be fabricated from transparent or translucent material, so as to allow viewing the position of the piston within the cartridge 16.

It should be noted that the description of the drug delivery device 5 as shown in FIG. 1 is merely illustrative. Other elements might be necessary in order to achieve full functionality. For example a dispense button and a drive mechanism can be present, which are configured to apply the adjusted dose value and move the piston in the distal direction such that the adjusted amount of the medical product is dispensed upon pressing the dispense button.

After administering a specific dose to the patient, it is usually required to remove the needle unit 20 from the drug delivery device 5, so as to prepare the drug delivery device 5 for the next application. During preparation, a new sterile needle unit 20 can be attached to the needle holder 24. In order to prevent contamination of the drug delivery device 5, a cap 30 is attached to the drug delivery device 5, which covers the distal end of the drug delivery device 5. The cap 30 may be a single injection moulded piece. The cap 30 comprises a retaining member 32 capable of securing the cap 30 by engaging with the housing 10, i.e. the body 12 or the cartridge holder 14. The cap 30 may be securable against axial and rotational movement with respect to the housing 10 by means of retaining member 32.

Making now reference to FIG. 2, the cap 30 and the distal part of drug delivery device 5 are shown in more detail.

In the embodiment shown in FIG. 2, the cap 30 comprises at a protruding element 34 on the inner surface 36 of the cap 30. The protruding element 34 abuts the needle unit 20 so as to prevent the retaining member from engaging with the housing. Accordingly, the retaining members 32 of the cap 30 are prevented from engaging with respect to the housing 10, as the cap 30 cannot reach its final position with respect to the housing 10. In this embodiment, the protruding element 34 is formed as a ring like step running along the inner side wall of the cap 30. However, other implementations, including a plurality of protruding elements are conceivable as well.

As shown in FIG. 2, the needle holder 24 comprises an outer thread 26, the outer thread 26 being capable of engaging with a corresponding inner thread 28 of the needle unit 20. Due to the threaded connection, the outer diameter of the needle unit 20 is significantly larger as compared to the outer diameter of the needle holder 24. Consequently, the protruding element 34 abuts the needle unit 20 in a region between the needle unit 20 and above the needle holder 24 in a radial direction.

In the embodiment shown in FIG. 2, the protruding element 34 is located in close proximity to the inner thread of the needle holder 24 in case the needle unit 20 is not attached to the needle holder 24. When the needle unit 20 is attached to the housing, the cap 30 encloses a cavity 38 along the inner surface 36 of the cap 30. The cavity 38 is capable of surrounding the needle unit 20 without abutting a needle 40 of the needle unit when attempting to engage the cap 30 on the cartridge holder 14 with the needle unit 20 being attached to the needle holder 24. Accordingly, no piercing through the cap 30 occurs when attempting to engage the cap 30 onto the housing 10.

Making now reference to FIG. 3, the cap 30 and the distal part of drug delivery device 5 are shown in more detail according to a further embodiment. As shown in FIG. 3, the cap 30 comprises a protruding element which is formed as a rib 50 on the inner side wall 36 of the cap 30. The rib 50 is arranged along a longitudinal axis 52 being arranged between the distal end 22 and a proximal end 54. It should be noted that a plurality of ribs 50 can be foreseen as well.

The ribs 50 of the cap 30 can be arranged such that they fit into respective grooves on the housing or the needle holder when attempting to engage the cap on the housing (not shown in FIG. 3). Hence, the ribs 50 provide an orientation feature which prevents users from placing the cap 30 in arbitrary orientations with respect to the housing 10. Mechanical cooperation of the ribs 50 and the respective grooves prevents rotation of the cap 30 with respect to the housing 10.

It should be noted that the protruding elements 34 or the ribs 50 shown in FIGS. 2 and 3 are merely illustrative. Other configurations, including a protruding element which abuts a front side of the needle unit 20 facing the distal end 22 of the drug delivery device 5 when the needle unit 20 is attached to the needle holder 24 are within of the scope of the invention.

Making now reference to FIG. 4, the cap 30 according to an embodiment similar to that depicted in FIG. 2 is shown in a cross sectional view. The cross section follows the line A-A' as indicated in FIG. 2. In the embodiment depicted in FIG. 4, the protruding element 34 is formed as a ring like step running around the inner side wall 36 of the cap 30.

Figure 5:
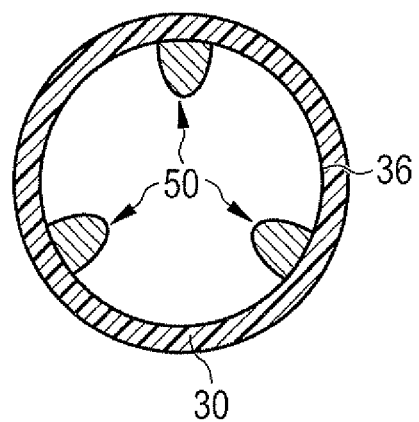
FIG. 5 schematically shows a cross sectional view of a part of a drug delivery device according to an embodiment, and FIG. 6 schematically shows a simplified side view of a drug delivery device according to an embodiment.

Making now reference to FIG. 5, the cap 30 according to an embodiment similar to that depicted in FIG. 3 is shown in a cross sectional view. The cross section follows the line B-B' as indicated in FIG. 3. In the embodiment depicted in FIG. 5, the protruding element is formed as three ribs 50 arranged along the longitudinal axis 52 between the proximal end and the distal end of the cap 30.

Figure 6:
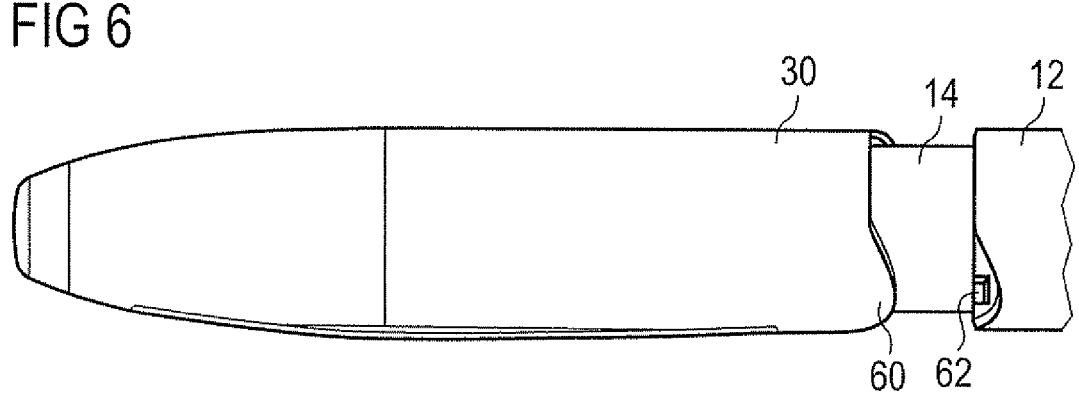

In FIG. 6, a further embodiment of the cap 30 comprises two protrusions 60 which are located at symmetric positions around the longitudinal axis 52. The protrusions can fit into corresponding depressions on the housing. Accordingly, the number of possible orientations of the cap 30 with respect to the housing is reduced. A retaining member may be arranged near the proximal end of the cap 30, in particular at the inner surface of the protrusions 60. The retaining member is capable of engaging into a corresponding mating retaining member on the housing 10. As shown in FIG. 6, the mating retaining member comprises a clip feature 62 or a clamp capable of engaging into a corresponding recess on the cap. However, other configurations including a clip feature or a clamp on the cap 30 and a corresponding recess on the housing are conceivable as well.

Other implementations are within the scope of the following claims. Elements of different implementations may be combined to form implementations not specifically described herein.

The invention claimed is:

1. A drug delivery device comprising:
a housing having a distal end comprising a needle holder having an outer surface with an outer diameter, where the outer surface is configured with a connector that engages a needle unit such that the needle unit is attached to the outer surface of the housing, where the needle unit has an outside diameter greater than the outer diameter of the needle holder and
a reusable cap having an inner surface and configured to cover the distal end of the housing and comprising a retaining member configured to engage and re-engage a corresponding mating member located proximate to the needle holder on the housing to secure the cap to the housing repeatedly when the needle unit is not attached to the housing, where the cap has a protruding element on the inner surface that extends radially inward a distance such that it contacts the needle unit when a user attempts to the replace the cap on the distal end of the housing to prevent the retaining member from engaging the corresponding mating member when the needle unit is attached to the needle holder thereby providing feedback to a user to remove the needle unit before the cap can be replaced on the housing, wherein the at least one protruding element is formed as either (i) a step along the inner side wall of the cap or (ii) at least one rib on the inner side wall of the cap, the at least one rib being arranged along a longitudinal axis being arranged between the distal end and the proximal end.

2. The drug delivery device according to claim 1, wherein the at least one rib on the inner side wall of the cap is capable of providing guidance when attempting to engage the cap on the housing.

3. The drug delivery device according to claim 1, wherein the needle holder is configured with a connector to allow attachment of the needle unit to the needle holder by rotating one relative to the other.

4. The drug delivery device according to claim 3, wherein the needle holder comprises an outer thread, the outer thread being capable of engaging with a corresponding inner thread of the needle unit.

5. The drug delivery device according to claim 3, wherein the needle connection means comprise a bayonet connection.

6. The drug delivery device according to claim 1, wherein the protruding element is arranged so as to contact the needle unit in a region between the outer diameter of the needle holder and the outer diameter of the needle unit.

7. The drug delivery device according to claim 1, wherein the protruding element abuts a front side of the needle unit facing the distal end of the drug delivery device when the needle unit is attached to the needle holder.

8. The drug delivery device according to claim 1, wherein the cap encloses a cavity along the inner surface of the cap.

9. The drug delivery device according to claim 8, wherein the cavity is capable of surrounding the needle unit without abutting a needle of the needle unit when attempting to engage the cap on the housing with the needle unit being attached to the needle holder.

10. The drug delivery device according to claim 9, wherein the retaining member is arranged on the end of the cap facing the proximal end of the housing.

11. The drug delivery device according to claim 9, wherein the retaining member is capable of engaging into a corresponding mating retaining member on the housing.

12. The drug delivery device according to claim 11, wherein the retaining member and the corresponding mating retaining member comprise a clip feature capable of engaging in a corresponding recess.

13. The drug delivery device according to claim 1, wherein the cap comprises at least one protrusion being arranged on an end face of the cap.

14. The drug delivery device according to claim 13, wherein the cap comprises two protrusions which are located at symmetric positions around a longitudinal axis being arranged between the distal end and the proximal end.

15. The drug delivery device according to claim 1, wherein the housing comprises a cartridge holder capable of enclosing a cartridge containing a medicament and wherein the cap can be attached such that it covers at least a part of the cartridge holder.

16. The drug delivery device according to claim 1, wherein the cap is a single injection moulded piece.

* * * * *